United States Patent [19]
Weiner et al.

[11] Patent Number: 5,834,014
[45] Date of Patent: *Nov. 10, 1998

[54] STIMULATION OF HAIR FOLLICLES

[75] Inventors: Norman Weiner, Ann Arbor, Mich.; Donald F.H. Wallach, Hollis, N.H.; Kamel Egbaria, Gurnee, Ill.; Ramachandran Chandrasekharan, Ypsilanti, Mich.

[73] Assignees: The Regents of the University of Michigan, Ann Arbor, Mich.; Micro-Pak, Inc., Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 539,865

[22] Filed: Oct. 6, 1995

[51] Int. Cl.$^6$ .............................. A61K 9/127; A61K 7/06
[52] U.S. Cl. ...................... 424/450; 424/70.1; 514/880; 514/881; 514/258; 514/260; 514/554
[58] Field of Search .......................... 626/450; 424/70.1; 514/880, 881, 258, 260, 557, 506, 554

[56] References Cited

U.S. PATENT DOCUMENTS

| | | | |
|---|---|---|---|
| 4,911,928 | 3/1990 | Wallach | 424/450 |
| 5,030,442 | 7/1991 | Uster et al. | 424/45 |
| 5,032,457 | 7/1991 | Wallach | 428/402.2 |
| 5,147,723 | 9/1992 | Wallach | 428/402.2 |
| 5,260,065 | 11/1993 | Mathur et al. | 424/450 |
| 5,422,370 | 6/1995 | Yu et al. | 514/557 |

OTHER PUBLICATIONS

Dowton, S.M., et al. "Influence of Liposomal Composition on Topical Delivery of Encapsulated Cyclosporin–A; An in Vitro Study Using Hairless Mouse Skin," *STP Pharma. Sci.,* 3: 404–407 (1993).

Hilchey, T., "Gene Gun Could Treat Hair Loss," *New York Times* (11 Jul. 1995).

Hu, Z., et al. "Topical delivery of Ciclosporin–A From Nonionic Liposomal Systems: An in Vivo/in Vitro Correlation Study Uaing Hairless Mouse Skin," *STP Pharma Sci.,* 4: 466–469 (1994).

Lieb, L., et al. "Follicular (Pilosebaceous Unit) Deposition and Pharmacological Behavior of Cimetidine as a Function of Formulation, " *Pharm. Res.,* 11: 1419–1423 (1994).

Niemiec, S.M., et al. "The Effect of Dosing Volume on the Disposition of Ciclosporin–A in Hairless Mouse Skin After Topical Application of a Nonionic Liposomal Formulation: An in Vitro Diifusion Study," *STP Pharma Sci.,* 4: 145–149 (1994).

Manosroi, A. et al., "Thermodynamic Characteristics of a Human Insulin–Deae–Dextran Complex Entrapped in Liposomes," *Drug Development and Industrial Pharmacy,* vol. 16, No. 5, 837–854 (1990).

*Primary Examiner*—Gollamudi S. Kishore
*Attorney, Agent, or Firm*—Lahive & Cockfield, LLP

[57] ABSTRACT

A novel method and delivery system for therapeutic weak acid or base materials has been developed. The method and delivery system utilize a therapeutic material which is modified to make it more hydrophilic and encapsulated in a lipid vesicle, preferably a non-phospholipid lipid vesicle. The method and delivery system is particularly well suited to topical delivery of minoxidil.

4 Claims, No Drawings

STIMULATION OF HAIR FOLLICLES

BACKGROUND OF THE INVENTION

The present invention concerns a preparation and method for topical administration of a drug into and/or through hair follicles. Using the preparation and method of the invention, significant amounts of weak acid or weak based drugs, e.g., minoxidil, may be delivered topically through the external skin surface.

The skin, particularly the horny layer, provides several functions including mechanical protection and a barrier against the transmittal of external substances into the internal tissues. However, this barrier effect causes difficulty in the topical administration of therapeutic drugs as well as unwanted substances. It has been generally accepted that the optimal means of transmitting drugs upon topical administration is through the lipid compartment of the stratum corneum. Accordingly, two general approaches to improve penetration through the lipid component have been devised; first, reducing the molecular weight of the drug provides easier access to the internal tissues; and second, partitioning the drug into a lipid phase as compared with an aqueous phase should allow easier penetration through the lipid component of the stratum corneum. While the first approach, reducing the molecular weight of the drug, has obvious advantages, it is often difficult to reduce the molecular weight without losing the activity of the drug. Therefore, much of the research on topical delivery of drugs has followed the second strategy, partitioning the drug into a lipid rather than an aqueous phase.

A number of different approaches have been attempted to achieve a favorable partition into the lipid rather than the aqueous phase. Since many of the drugs are either weak acids or bases, making the formulation at a pH such that the drug is in an unionized state where the solubility in the aqueous phase is normally decreased has been considered a preferable mode. Similarly, encapsulating a drug in a lipophilic rather than hydrophilic phase has potential advantageous properties. This lipophilic phase can include lipid vesicles such as liposomes and lipid structures such as micelles.

Accordingly, it has been theorized that the use of liposome should be a particularly advantageous in delivering drugs through the stratum corneum. Much of the earlier work on liposomes, particularly those using phosphotidylcholine and phosphotidylserine as the wall materials, were attempts to simulate cellular membranes. The theory is that if one provides a drug to the skin in lipid systems similar to cellular membrane that is similar to the skin cells, the transition from the model system through the skin membranes, passage from this system through the skin should be facilitated. However, the use of liposomes as drug delivery vehicles have not normally improved drug permeation through the skin. Further, the amount of hydrophobic drug deposited into the dermis using liposomes has, in fact, been found to be lower than that obtained using simple solutions. Extensive in vivo and in vitro experiments on the penetration into the skin of various hydrophobic drugs such as progesterone, estradiol, hydrocortisone and cyclosporin-A after topical administration of drugs and liposomal formulas has shown that phospholipid liposomes do not improve penetration. Accordingly, conventional wisdom does not work in this type of system.

An example of a drug that has been problematic for topical delivery is minoxidil, 6-(1-Piperidinyl)-2,4-pyrimidinediamine 3-oxide. Minoxidil was originally used as a hypertensive agent so it was not generally used topically. However, it has recently been shown that topical solutions of minoxidil, sold under the trademark Rogaine®, act as a hair growth stimulant. Rogaine is a 2% solution of minoxidil in an alcohol/propylene glycol/water mixture. Minoxidil is almost insoluble in acetone, chloroform, water or ethyl acetate. Although there is some penetration of the skin surface and hair follicles using this alcohol based solution of minoxidil, a way to improve its penetration should make a more effective hair growth preparation.

Accordingly, an object of the invention is to provide a method of providing better penetration into and across skin, and particularly into the hair follicles for topically administered drugs.

A further object of the invention is to provide a method and preparation which provides good penetration across skin through hair follicles in higher quantities than is presently known.

Another object of the invention is to provide a minoxidil preparation which has improved penetration into the hair follicles.

These and other objects and features of the invention will be apparent from the following description and the drawing.

SUMMARY OF THE INVENTION

The present invention features a method of improving topical penetration of a therapeutic material such as a drug through the skin. The invention is based, in part, on the discovery that making a material hydrophilic, rather than hydrophobic, and encapsulating the drug in a lipid vesicle, can improve delivery. This is particularly pertinent to the delivery of minoxidil. Non-phospholipid lipid vesicles, particularly those having glycerol dilaurate as the primary lipid in the wall material, are preferred.

For a number of therapeutic materials, topical penetration of these materials into a skin portion having hair follicles can be improved by modifying the solubility of the therapeutic materials in aqueous solutions. The modified therapeutic material is encapsulated in a lipid vesicle and the lipid vesicle is delivered to the skin portion having hair follicles, whereby the hair follicles appear to act as a conduit for the therapeutic material.

A number of different modifications can be made to the therapeutic material to provide the advantages of the invention. One such modification is ionizing the material by modifying the pH of a solution containing the material. Ionization improves aqueous solubility. Similarly, the therapeutic material may be converted into a salt preferably by a reaction of the therapeutic material with an organic acid or base, most preferably an alpha-hydroxy acid such as lactic acid or a pharmaceutically acceptable derivative thereof. In other aspects, the salt could be made by reacting the therapeutic material with a dextrin such as a cyclodextrin.

As noted, preferred lipid vesicles are non-phospholipid lipid vesicles. These lipid vesicles are well known in the art and are described in patents such as U.S. Pat. No. 4,911,928, U.S. Pat. No. 5,032,457, and U.S. Pat. No. 5,147,723, the disclosures which are incorporated herein by reference. U.S. Pat. No. 5,260,065, the disclosure of which is also incorporated herein by reference, describes a preferred type of lipid vesicle. This patent describes lipid vesicles having blended lipid walls with a primary walled material selected from the group consisting of $C_{12}$–$C_{18}$ fatty alcohols, $C_{12}$–$C_{18}$ glycol monoesters, and $C_{12}$–$C_{18}$ glycerol mono and diesters. These materials appear to have particular potency in directing the modified therapy of materials through the hair follicles. As noted previously, the preferred therapeutic material is minoxidil or a therapeutically effective derivative thereof. Using the minoxidil, the preferred wall material for vesicles has glycerol dilaurate as a primary lipid and polyoxyethylene 10 stearyl ether as a secondary wall material. The vesicles also may include cholesterol, phytosterol, or pharmaceutically acceptable derivatives thereof. The preferred active is a reaction product of minoxidil and lactic acid (or lactate) which appears to have particular effectiveness. This minoxidil product acts as a pharmaceutical preparation for treatment of hair loss with advantageous effects.

The following description will more fully elucidate the invention.

DETAILED DESCRIPTION OF THE INVENTION

The present invention features the preparation and method for improved uptake of therapeutic materials by topical administration. The invention is particularly pertinent to delivery of minoxidil and other similar weak acids or weak bases. The invention is based, in part, on the discovery that by making these materials more hydrophilic, improved penetration through hair follicles could be achieved while minimizing the uptake by the lipid bilayer regions of the horny layer of the skin. This is contrary to standard topical delivery concepts which say that the material should be made more hydrophobic so they are transmitted easier through the lipid compartment of the stratum corneum.

The method and preparation of the invention use lipid vesicles, primarily non-phospholipid lipid vesicles, to achieve this improved penetration. First, the materials themselves are modified to make them more hydrophilic by reacting them with an acid or base, e.g., an organic acid or base such as lactic acid. In fact, the use of hydrophobic materials in lipid vesicles is contraindicated since they do not penetrate as well as the hydrophilic materials.

Another possible way of making the materials more hydrophilic is by placing them in a pH where they are ionized and therefore become more water soluble. That water-soluble material are transported to a greater extent by association with nonionic vesicles has been tested using carboxyfluoroscein, TGF-α, interferon, and oligonucliotides. The present invention has particular usefulness in treating skin diseases of a follicular nature, such as acne, alopecia arreata and, using minoxidil, male pattern baldness. In addition, diseases without follicular involvement could be treated since the follicles could be used to transport the drugs to other regions of the dermis.

The mechanism for this delivery system appears to be the partitioning of the drugs from the liposomal lipid bilayers into the skin after dehydration. This may account for the retardation of hydrophobic drug deposition into the skin, since the hydrophobic drugs stay in the lipid bilayer rather than penetrating the hair follicles.

The following examples more clearly illustrate the invention.

EXAMPLE 1

In this example, an oligonucleotide having a $pK_a$ of about 9 is modified using a change in pH. The permeation of a charged drug across the stratum corneum is negligible if the skin lacks follicles, and there is only transport via the follicular route when the follicles were present. The material is encapsulated in a phospholipid lipid vesicle (or liposome) and the pH of the formulation was adjusted to 10–11. The liposomes were made with phosphatidylcholine, cholesterol and phosphatidylserine a molar ratio of 1:05:0.1 and total lipid concentration of 25 mg/ml. The results show that deposition of the oligonucleotide into the dermal layers is much higher at pH 10–11 than it is at either pH 7.4 or pH 3 in a buffered liposomal system. The amounts in the dermis of skin specimens with follicles were always much larger than those found in the dermis of skin without follicles. Accordingly, it clear that the follicular route is effective for transportation of hydrophilic materials in lipid vesicles across the stratum corium.

EXAMPLE 2

In this example, phospholipid-based liposomes containing minoxidil were tested for stimulation of hair growth on balding stumptail Macaque monkeys. Minoxidil is very insoluble in water, organic solvents and oils. Conventional minoxidil preparations utilize a mixture of alcohol, propylene glycol, and water.

Balding stumptail Macaque monkeys were treated for sixteen weeks with liposomes which contained minoxidil, a standard alcohol/propylene glycol/water preparation, or controls which included the liposomes or the preparation but did not contain minoxidil. Each monkey was treated once per day (5 days/week) on a one inch square of balding skin. The areas were shaved, the hair was collected, and weighed at four week intervals.

Statistically significant changes in the hair weight was found using both the standard alcohol minoxidil preparation and the liposomal preparation as compared to the controls. The standard alcohol preparation appeared to provide better hair growth but the difference was not statistically significant.

Accordingly, this shows that minoxidil can be released from lipid vesicles such as liposomes.

EXAMPLE 3

In this example, a variety of formulations were tested in order to determine the most efficacious formulation for delivering minoxidil. Table 1 shows the formulations used in this testing and the initial results.

TABLE 1

| | FORMULATIONS | SURFACE & STRATUM CORNEUM | LIVING SKIN STRATA | RECOVERY |
|---|---|---|---|---|
| I | GDL/HPBCD NOVASOMES | 96.39 ± 0.37 | 0.21 ± 0.05 | 96.62 ± 0.32 |
| II | GDL/HPBCD/ETOH NOVASOMES | 90.85 ± 4.16 | 0.36 ± 0.11 | 91.17 ± 4.14 |
| III | GDL/LACTATE NOVASOMES | 92.76 ± 3.89 | 0.75 ± 0.33 | 93.51 ± 3.56 |
| IV | GDS/HPBCD NOVASOMES | 96.21 ± 6.14 | 0.09 ± 0.03 | 96.30 ± 6.14 |
| V | GDS/HPBCD/ETOH NOVASOMES | 98.89 ± 2.23 | 0.18 ± 0.05 | 98.87 ± 2.20 |

TABLE 1-continued

| FORMULATIONS | | SURFACE & STRATUM CORNEUM | LIVING SKIN STRATA | RECOVERY |
|---|---|---|---|---|
| VI | GDS/LACTATE NOVASOMES | 90.63 ± 5.82 | 0.22 ± 0.03 | 90.86 ± 5.84 |
| VII | GDL/GDS/HPBCD NOVASOMES | 84.41 ± 7.73 | 0.11 ± 0.01 | 84.52 ± 7.72 |
| VIII | GDL/GDS/HPBCD/ETOH NOVASOMES | 92.96 ± 6.01 | 0.24 ± 0.05 | 93.20 ± 6.02 |
| IX | HPBCD AQUEOUS SOLUTION | 94.44 ± 3.30 | 0.08 ± 0.03 | 94.52 ± 3.27 |
| X | HPBCD/ETOH AQUEOUS SOLUTION | 99.10 ± 8.99 | 0.10 ± 0.02 | 99.21 ± 9.01 |
| XI | LACTATE AQUEOUS SOLUTION | 92.99 ± 6.51 | 0.18 ± 0.01 | 93.17 ± 6.51 |
| XII | ROGAINE | 86.45 ± 2.79 | 0.35 ± 0.14 | 86.80 ± 2.66 |

Deposition of minoxidil (expressed as percent of applied does±standard deviation) into various compartments of hairless rat skin 12 hours after in vivo topical application of 100 $\mu$l various formulations to 2.54 cm$^2$ area (n=3–4).

In all formulations, the vesicles were made with a 57:15:28 ratio of primary lipid/cholesterol/secondary lipid. Formula I had vesicles made of glycerol dilaurate (primary lipid), polyoxyethylene 10 stearyl ether (secondary lipid), and cholesterol, with minoxidil formed into a salt with a cyclodextrin (HPBCD). Formula II had the same vesicles and minoxidil, except ethanol was included in the minoxidil formulation. Formula III had the same vesicles with a salt made of the minoxidil using lactic acid/lactate as the salt forming agent. Formula IV is the same as Formula I except the glycerol dilaurate is replaced with glycerol distearate. Formula V is identical to Formula II but, again, the glycerol distearate replaces the glycerol dilaurate. Formula VI is the same as Formula III but again, the glycerol dilaurate is replaced with glycerol distearate. Formula VII has a combination of glycerol dilaurate and glycerol distearate in equal parts as the vesicle forming agent and is otherwise the same as Formula I, while Formula VIII is the same as Formula II except the glycerol dilaurate/glycerol distearate combination is used to replace the glycerol dilaurate. Formula IX is an aqueous solution of the cyclodextrin cross-linking agent with the minoxidil so as identical to Formulas I, IV and VII but without the lipid vesicle encapsulation. Formula X is the same as Formulas II, V and VIII except it is lacking the vesicles. Formula XI is the same as Formula III except lacking the vesicles and Formula XII is of an identical composition to the commercial Rogaine® preparation which does not have a minoxidil salt but rather as a solution of minoxidil in a combination of ethanol, propylene glycol and water. This preparation is considered to be the best for delivering minoxidil to hair follicles.

Table 1 shows the deposition of minoxidil (expressed as percent of applied dose±standard deviation) into various components of hairless rat skin 12 hours after in vivo topical application of 100 ml of the various formulations to a 2.54 cm$^2$ area. As can be seen from the data shown on this table, Formula III, the glycerol dilaurate/lactic acid vesicles had twice the penetration into the deepest skin strata of any other formulation. The next best were the commercial Rogaine® preparation and the preparation having the cyclodextrin salt and ethanol oxide. What is most interesting is that a simple change from glycerol dilaurate ($C_{12}$) to glycerol distearate ($C_{18}$) in the vesicle wall changes the penetration several fold.

To test the formulations, 100$\mu$l of the formulation including $^3$H-radiolabeled minoxidil is applied to a 2.54 cm$^2$ area of dorsal rat skin. Three to four rats were used for each formulation. At the end of 12 hours, the rat is sacrificed and the minoxidil on the skin surface is harvested by swabbing the skin with water and alcohol/water washes. The stratum corneum is segregated from the rest of the skin by repeated use of scotch tape; the scotch tape stripping the stratum corneum and allowing harvesting of the minoxidil. The minoxidil in the living skin strata (the living epidermis and dermis) is harvested by surgically removing the remainder of the skin under the surface of application and separating the layers. Each of the samples is segregated and a scintillation counter is used to determine the amount of minoxidil.

Table 2 shows that similar results were obtained in tests using various formulations which were deposited into pilosebaceous of hamster ears. The test uses a 50 $\mu$l topical deposition of the formulation onto the hamster ear, and 30 hours thereafter, the pilosebaceous ventral dermis, cartilage and dorsal ear are measured for minoxidil. More particularly, male Syrian hamsters are cyclically provided 14 hours of light and 10 hours of darkness to maximize androgen dependent sebaceous gland activity and control the size of the glands. Food and water is given to the hamsters ad libitum. The animals are anesthetized with 1 ml of a 10 mg/ml phenobarbital solution.

The test formulation is applied to the ventral side of the ear, typically in 50 $\mu$l doses. The anesthetization is strengthened every two hours, and 3–4 animals are used in each group. The area of the ear exposed to treatment is biopsied with a 8–10 mm circular punch, rinsed with 5 ml HEPES buffer, blotted with tissue, and rinsed with an additional 5 ml of buffer. The full thickness biopsy is then peeled carefully into its constituent layers using forceps. The epidermis is peeled off easily by probing the edge of the membrane with forceps, clamping a loose end, and pulling. The sebaceous glands in the ventral dermis and the cartilage are scraped free with a dull scalpel so as to avoid damage to the surrounding dermis. The pilosebaceous material is removed by first placing the ventral dermis on a glass slide, dermis side up, and scraping more intensely than for cartilage removal. A milky white suspension is collected.

Table 2 shows percentages and, for pilosebaceous region shows actual $\mu$l recovered.

TABLE 2

| Ear Compartment | Formulation Type | | | |
| --- | --- | --- | --- | --- |
| | Formula XII-(Rogaine) | Formula I-(Novasome/Cylclodextran) | Formula II-(I + alcohol) | Formula III-(Novasome) |
| Pilosebaceous | 0.1 ± 0.1 | 0.2 ± 0.1 | 0.2 ± 0.1 | 0.4 ± 0.1 |
| ($\mu$g) | (2.65 ± 1.27) | (3.14 ± 1.30) | (4.37 ± 1.92) | (7.54 ± 1.96) |
| Ventral Dermis | 0 | 0 | 0 | 0 |
| Cartilage | 0.3 ± 0.2 | 0.4 ± 0.5 | 0.3 ± 0.1 | 1.8 ± 1.1 |
| Dorsal Ear | 0.5 ± 0.5 | 0.2 ± 0.2 | 0.2 ± 0 | 1.7 ± 0.7 |

The formulations used were formulas I, II, III and XII as described previously. As can be seen from the results shown on Table 3, Formula III yields much higher levels of minoxidil in the pilosebaceous, cartilage and dorsal ear than any of the other formulations. The other formulations, while not as good as Formulation III, are all comparable to the Rogaine® formulation XII which is the best commercial formulation for the delivery of minoxidil. Accordingly, any of these formulations would be acceptable.

The foregoing examples illustrate the effectiveness of the present invention. These examples are merely exemplary and those skilled in the art will be able to determine other modifications to the described procedures which fall within the scope of the invention. Accordingly, the invention is defined by the following claims and equivalents thereof.

We claim:

1. A method of providing improved topical penetration of minoxidil, comprising the steps of:

combining minoxidil with an alpha-hydroxy acid, thereby forming a modified minoxidil which is more hydrophilic than said unmodified minoxidil;

encapsulating said modified minoxidil in a lipid vesicle having glycerol dilaurate as a primary wall component; and delivering said encapsulated modified minoxidil to a skin portion having hair follicles, such that said minoxidil topically penetrates the skin portion having hair follicles.

2. The method of claim 1, wherein said alpha-hydroxy acid comprises lactic acid or a pharmaceutically acceptable salt thereof.

3. The method of claim 1, wherein said lipid vesicle further comprises polyoxyethylene 10 stearyl ether.

4. The method of claim 3, wherein said lipid vesicle further comprises cholesterol or phytosterol.

* * * * *